(12) United States Patent
Zierhofer et al.

(10) Patent No.: US 7,941,223 B2
(45) Date of Patent: May 10, 2011

(54) COCHLEAR IMPLANT STIMULATION WITH VARIABLE NUMBER OF ELECTRODES

(75) Inventors: Clemens M. Zierhofer, Kundl (AT); Peter Nopp, Birgitz (AT); Peter Schleich, Igls (AT); Andrea Nobbe, München (DE); Ernst Aschbacher, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 857 days.

(21) Appl. No.: 11/872,983

(22) Filed: Oct. 16, 2007

(65) Prior Publication Data

US 2008/0172108 A1 Jul. 17, 2008

Related U.S. Application Data

(63) Continuation-in-part of application No. 11/076,446, filed on Mar. 8, 2005, now Pat. No. 7,283,876.

(60) Provisional application No. 60/551,318, filed on Mar. 8, 2004.

(51) Int. Cl.
*A61N 1/18* (2006.01)
(52) U.S. Cl. ............... 607/56; 607/55; 607/57; 607/137
(58) Field of Classification Search .................... 607/55, 607/56, 57, 137
See application file for complete search history.

(56) References Cited

U.S. PATENT DOCUMENTS

| 4,515,158 | A | 5/1985 | Patrick et al. | 128/419 R |
| 6,584,525 | B1 | 6/2003 | Klingman | 701/118 |
| 6,778,858 | B1 * | 8/2004 | Peeters | 607/57 |
| 7,742,819 | B2 * | 6/2010 | Moffitt | 607/46 |
| 2001/0031909 | A1 | 10/2001 | Faltys et al. | 600/25 |
| 2003/0114899 | A1 * | 6/2003 | Woods et al. | 607/60 |
| 2004/0082985 | A1 | 4/2004 | Faltys et al. | 607/116 |
| 2005/0107843 | A1 | 5/2005 | McDermott et al. | 607/57 |
| 2005/0203589 | A1 | 9/2005 | Zierhofer | 607/57 |
| 2006/0052841 | A1 | 3/2006 | Daly et al. | 607/57 |
| 2006/0265061 | A1 | 11/2006 | Kwon et al. | 623/10 |
| 2007/0156202 | A1 | 7/2007 | Zierhofer | 607/57 |

(Continued)

FOREIGN PATENT DOCUMENTS

WO WO 99/49815 10/1999

(Continued)

OTHER PUBLICATIONS

McKay, Colette, et al, "The effect of rate of stimulation on perception of spectral shape by cochlear implantees", *Journal of Acoustical Society of America*, AIP/Acoustical Society of America, Melville, NY, US, vol. 118; No. 1; Jan. 1, 2005, pp. 386-392; XP012073185; ISSN: 001-4966.

(Continued)

*Primary Examiner* — Carl H Layno
*Assistant Examiner* — Natasha N Patel
(74) *Attorney, Agent, or Firm* — Sunstein Kann Murphy & Timbers LLP (57) ABSTRACT

A system and method for activating electrodes in an implanted electrode array with a stimulation signal is described. A stimulation definition stage, for each of a plurality of defined sound signal characteristics (C), assigns each electrode to one of a plurality of stimulation groups (G) each having an associated group stimulation amplitude function (A), where (G) varies with (C). An electrode stimulator activates each electrode as the stimulation signal varies based on spectral components of the stimulation signal.

21 Claims, 4 Drawing Sheets

U.S. PATENT DOCUMENTS

2007/0225776 A1    9/2007    Fritsch et al. .................. 607/57

FOREIGN PATENT DOCUMENTS

| WO | WO 01/19135 A1 | 3/2001 |
| WO | WO 01/19304 A1 | 3/2001 |
| WO | WO 2005/113064 A | 12/2005 |
| WO | WO 2006/119069 | 11/2006 |

OTHER PUBLICATIONS

Secker-Walker, H., et al, "Time-domain analysis of auditory-nerve-fiber firing rates", *J. Acoust. Soc. Am.* 88(3), pp. 1427-1436 (1990).

Wilson, B.S., et al, "Temporal Representations With Cochlear Implants", *Am. J. Otology*, vol. 18, No. 6 (Suppl), S30-S34, (1997).

Wilson, B.S., et al, "Comparative Studies of Speech Processing Strategies for Cochlear Implants", *Laryngoscope* (1998); pp. 1069-1077.

Ziese, M., et al, "Speech Understanding with the CIS and the n-ofm Strategy in the MED-EL COMBI 40+ System", *ORL* 2000:62:321-329.

International Search Report dated Nov. 16, 2005 from corresponding U.S. Appl. No. 11/076,446.

International Search Report dated Jan. 27, 2009, PCT/US2008/079923.

* cited by examiner

COCHLEAR IMPLANT STIMULATION WITH VARIABLE NUMBER OF ELECTRODES

This application is a continuation-in-part of co-pending U.S. application Ser. No. 11/076,446, filed Mar. 8, 2005, which in turn claimed priority from U.S. Provisional Patent Application 60/551,318, filed Mar. 8, 2004; the contents of all of which are hereby incorporated by reference.

FIELD OF THE INVENTION

The present invention relates to implant electrode stimulation, and more particularly, a stimulation strategy that varies the number of electrodes stimulated.

BACKGROUND ART

Cochlear implants can provide hearing to profoundly deaf or severely hearing impaired persons. Unlike conventional hearing aids which mechanically apply an amplified sound signal to the middle ear, a cochlear implant provides direct electrical stimulation to acoustic nerve in the inner ear. Of course, it is desired that the created hearing sensation be as natural as possible.

Figure 1:
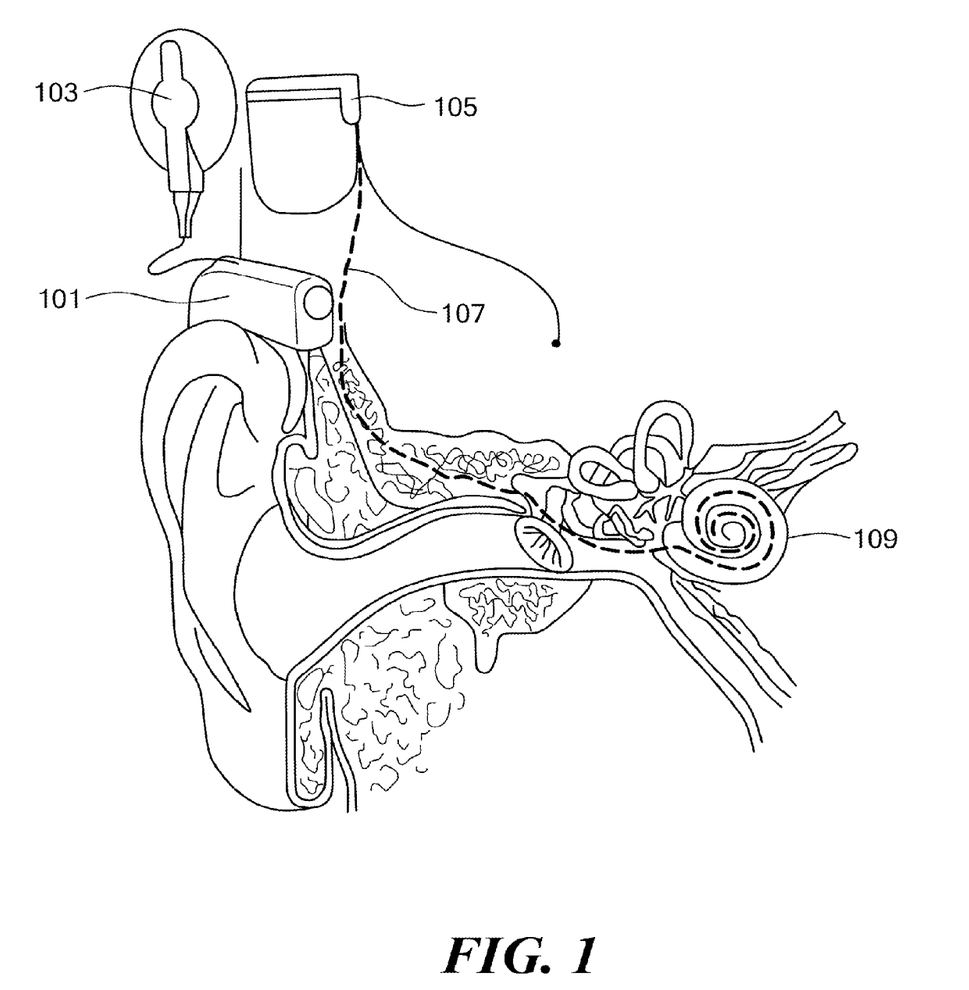
FIG. 1 shows a typical cochlear implant system.

FIG. 1 shows a typical cochlear implant system. An external speech processor 101 that is positioned by the outer ear. The speech processor 101 typically includes a power supply (batteries) for the entire system and performs signal processing of the acoustic signal to extract the stimulation parameters for the implanted elements of the system. An implanted stimulator 105 generates a stimulation signal in the form of electrical pulses that are sent to electrodes in an implanted electrode array 107 that extends into the scala tympani 109 in the inner ear. Activation of the electrodes with the pulses stimulates the adjacent audio nerve tissue. The speech processor 101 communicates data and power to the stimulator 105 by transcutaneous radio frequency link between primary coils 103 and corresponding secondary coils within the stimulator 105 (or alternatively by a percutaneous plug in the skin).

In cochlear implants today, a relatively small number of electrodes is each associated with relatively broad frequency bands, with each electrode addressing a group of neurons through a stimulation pulse the charge of which is derived from the instantaneous amplitude of the envelope within that frequency band. In some coding strategies, stimulation pulses are applied at constant rate across all electrodes, whereas in other coding strategies, stimulation pulses are applied at an electrode-specific rate.

One problem in cochlear implants is spatial channel interaction. Spatial channel interaction means that there is considerable geometric overlapping of electrical fields at the location of the excitable nervous tissue, if different stimulation electrodes (positioned in the scala tympani) are activated. Thus the same neurons are activated if different electrodes are stimulated. Spatial channel interaction is primarily due to the conductive fluids and tissues surrounding the stimulation electrode array.

At present, the most successful stimulation strategy is the so called "continuous-interleaved-sampling strategy" (CIS) introduced by Wilson B S, Finley C C, Lawson D T, Wolford R D, Eddington D K, Rabinowitz W M, *Better Speech Recognition with Cochlear Implants*, Nature, vol. 352, 236-238, July 1991, which is hereby incorporated by reference. Signal processing for CIS in the speech processor typically involves the steps of:

(1) splitting up of the audio frequency range into spectral bands by means of a filter bank;
(2) envelope detection of each filter output signal; and
(3) instantaneous nonlinear compression of the envelope signal (map law).

According to the tonotopic organization of the cochlea, each stimulation electrode in the scala tympani is associated with a band pass filter of the external filter bank. For stimulation, symmetrical biphasic current pulses are applied. The amplitudes of the stimulation pulses are directly obtained from the compressed envelope signals (step (3) above). These signals are sampled sequentially, and the stimulation pulses are applied in a strictly non-overlapping sequence. Thus, the problem of spatial channel interaction is defused and a comparatively precise definition of electrical fields in the cochlea is achieved. For example, consider a 12-channel CIS-system with a maximum overall stimulation rate of 18 kpps. Assuming that each channel is addressed once in a cycle, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 µs, which approaches the lower limit.

A stimulation strategy related to CIS is the "N-of-M" strategy, wherein only the N electrode channels with maximum energy are selected out of the total number of M channels during each stimulation cycle, as described by Wilson B S, Finley C C, Farmer J C, Lawson D T, Weber B A, Wolford R D, Kenan P D, White M W, Merzenich M M, Schindler R A, *Comparative Studies Of Speech Processing Strategies For Cochlear Implants*, Laryngoscope 1998; 98:1069-1077, which is hereby incorporated by reference. Typically, number M is constant and equal to the overall number of usable channels. Thereby the instantaneous stimulation rate of a selected channel is increased by a factor of M/N. Interestingly, N of M strategies do not seem not to improve speech perception as compared to standard CIS, as described in Ziese M, Stützel A, von Specht H, Begali K, Freigang B, Sroka S, Nopp P, *Speech Understanding With CIS And N-Of-M Strategy In The MED-EL COMBI 40+ System*, ORL 2000; 62:321-329, which is hereby incorporated by reference.

One disadvantage of N-of-M strategies (with constant M) is that neurons or ensembles of neurons may suffer "microshocks", if electrode channels are switched from "inactive" to "active". For example, consider a situation where a train of supra-threshold pulses is switched on at a particular electrode. The initial pulse in the train will cause action potentials in the majority of neurons that are close to the electrode, followed by a refractory period in which a more limited neural response can be elicited. The majority of the neurons will continue to be at similar refractory states, until sufficient time has passed to cause a sufficient distribution of refractory states. Thus, for at least an initial period of time, the majority of neurons will respond in the same manner to each pulse due to their similar refractory state, as described by Wilson B S, Finley C C, Farmer J C, Lawson D T, Zerbi M, *Temporal Representation With Cochlear Implants*, Am. J. Otology, Vol. 18, No. 6(Suppl), S30-S34, 1997, which is hereby incorporated by reference.

In standard CIS, periods with no activity at particular electrodes do not occur, since each electrode is stimulated in each cycle, and minimum pulse amplitudes are usually close to or slightly above thresholds. So even when there is no spectral energy present in a particular frequency band, the associated electrode will be active, keeping neurons in different refractory states. Additionally, a number of neurons may be kept busy because of activity of neighboring channels. In this respect, spatial channel interaction can have an (unintentional) advantageous effect.

SUMMARY OF THE INVENTION

Embodiments of the present invention are directed to systems, methods and computer program products for activating electrodes in an implanted electrode array with a stimulation signal. Although the specific description is presented with regards to a cochlear implant system, the invention is not limited by that example and may be equally useful in other implant systems that use electrode stimulation. In the described embodiments, a stimulation definition stage, for each of a plurality of defined sound signal characteristics (C), assigns each electrode to one of multiple stimulation groups (G) which each have an associated group stimulation amplitude function (A), where (G) varies with (C). An electrode stimulator activates each electrode as the stimulation signal varies based on spectral components of the stimulation signal.

In further specific embodiments, the activating of each electrode may further be based on electrode location and/or a stimulation group pulse rate defined for each stimulation group. And the group stimulation amplitude function (A) for each stimulation group may have a constant value, or reflects non-linear response characteristics of tissue stimulated by each electrode, and/or reflect spatial interaction between the electrodes. In a specific embodiment, the implanted electrode array may be part of a cochlear implant system.

DETAILED DESCRIPTION OF SPECIFIC EMBODIMENTS

Embodiments of the present invention are direct to techniques for activating electrodes in an implanted electrode array. As compared to Continuous-Interleaved-Sampling (CIS) approaches, higher stimulation rates can be used while avoiding, for example, "micro-shocks" encountered in an N-of-M strategy.

Figure 2:
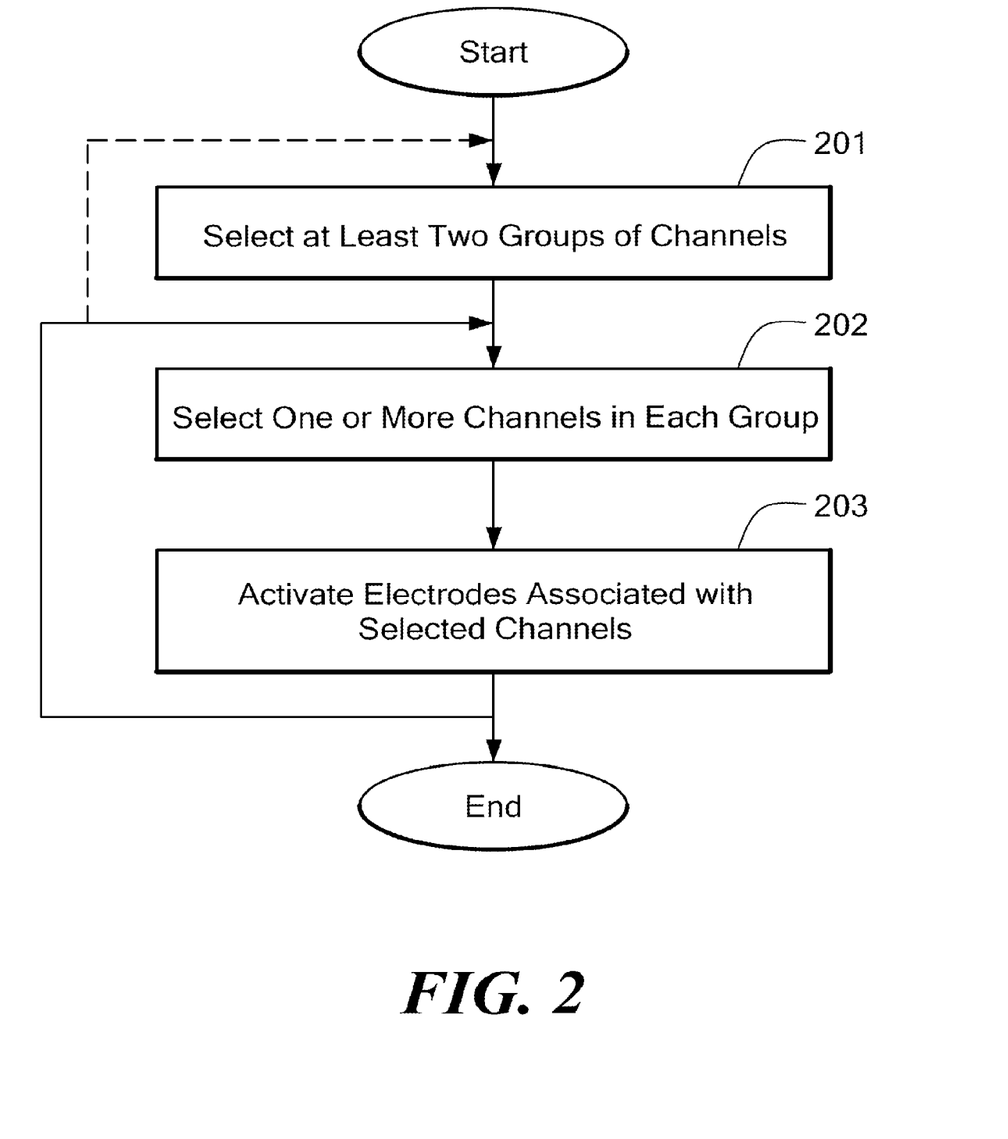
FIG. 2 is a flow chart illustrating a method for activating electrodes in a multi-channel electrode array, in accordance with an embodiment of the invention.

FIG. 2 is a flow chart showing various steps in activating electrodes in a multi-channel electrode array, in accordance with an embodiment of the invention. The multi-channel electrode array 107 may be part of, without limitation, a cochlear implant having two parts—speech processor 101 and implanted stimulator 105 (see FIG. 1). Specific embodiments may be based on a monopolar electrode configuration in which a remote ground electrode is used, or in a bipolar configuration in which each active electrode has a corresponding reference electrode. A controller may be integrated into speech processor 101 and/or stimulator 105 which controls activation of the electrodes, and the controller may include, without limitation, a circuit and/or a processor that may be pre-programmed or configured to be loaded with an appropriate program for activation of the electrodes.

Each processing channel is typically, although not necessarily, associated with a different electrode in the array 107, and also may be associated with a band pass filter, envelope detector, and/or a compressor. The band pass filter may be part of a filter bank located in the speech processor 101, which splits a received audio signal into spectral bands. The output of the band pass filter may undergo further signal processing, such as envelope detection and compression. The amplitudes of the stimulation pulses, provided by the implanted stimulator 105 and used to active the channel's associated electrode are typically a function of the compressed envelope of the channel's filter output signal. For example, the basic stimulation waveform is a symmetrical, biphasic pulse.

Referring back to FIG. 2, in illustrative embodiments of the invention at least two groups of channels are selected (hereinafter "selected groups"), wherein at least one selected group has multiple channels, step 201. The selected groups may be predefined, and stored for example, in a memory device such as a diskette, a fixed disk, a Compact Disk (CD), Read Only Memory (ROM), Erasable Programmable Read-Only Memory (EPROM), and/or Random Access Memory (RAM). As described in more detail in Example 3 below, the selected groups may be selected such that the spatial channel interaction between the channels in a selected group ensures constant activity in all cochlear areas.

In step 202, at least one channel within each group is selected as a function of any suitable criteria. For example, the selection may be based on the filter output amplitudes associated with the given channels in the group. In various embodiments, the channels in the groups that have the maximum amplitude may be selected. The electrodes of the selected channels are then activated in step 203. The electrodes of the selected channels may be activated sequentially or simultaneously. In the latter case, numerical methods of "channel interaction compensation," may be used, as known in the art and described in U.S. Pat. No. 6,594,525, which is hereby incorporated by reference. The steps of selecting at least one channel in each selected group and activating the electrodes associated with each selected channel are repeated, such that that the selected channels in at least one selected group varies. In various embodiments, the selected groups may also vary between stimulation cycles based on any suitable criteria (illustrated by the dotted line in FIG. 2).

The following examples describe a 12-channel system with sequential and/or parallel stimulation, where the electrode addresses are within the range [1-12]. Pulses with equal phase durations and a maximum pulse repetition rate R is assumed. Selected groups are represented within brackets, and the index after the closing bracket represents the number of selected maximum channels a within the group, and whether the selected channels are activated sequentially "s" or in parallel "p" (i.e., simultaneously).

EXAMPLE 1

Prior Art—"Conventional CIS"

Figure 3:
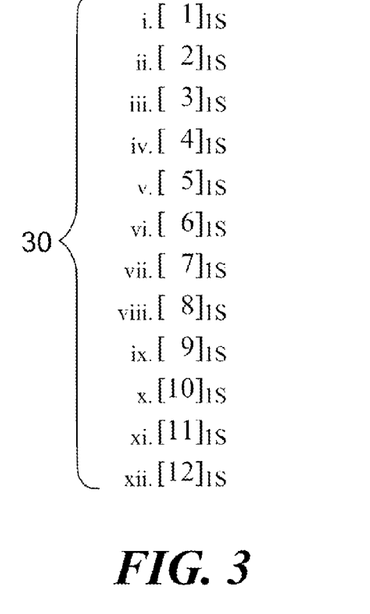
FIG. 3 shows an example of selected groups in a conventional CIS system (Prior Art).

In Example 1, selected groups in a conventional CIS system are shown in FIG. 3 (Prior Art). One CIS-stimulation cycle includes 12 selected groups 30. Each selected group 30 is composed of one channel. Since only one channel is present, it is the maximum itself (trivial case). Thus, this setting represents standard 12-channel CIS. The cycle repetition rate is R/12.

EXAMPLE 2

Prior Art—"N-of-M"

Figure 4:
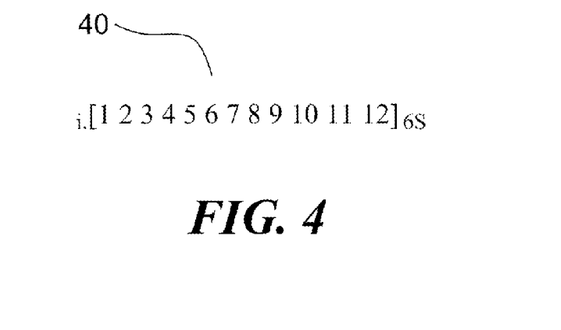
FIG. 4 shows an example of selected groups based on an N-of-M strategy (Prior Art).

In Example 2, one stimulation cycle using an N-of-M strategy contains only one selected group 40, which is composed of all 12 channels, as shown in FIG. 4 (Prior Art). The six channels with maximum energy are selected. Thus, this setting represents a conventional 6-of-12 setting. The cycle repetition rate is R/6, which is an enhancement by a factor of 2 as compared to Example 1.

EXAMPLE 3

Figure 5:
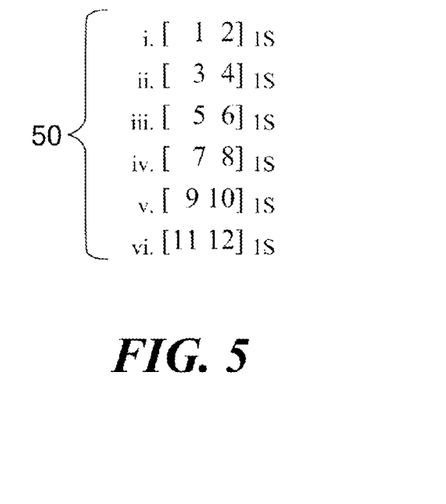
FIG. 5 shows an example of selected groups providing constant activity in all cochlear regions.

In Example 3, one stimulation cycle contains six selected groups 50, as shown in FIG. 5 in accordance with an embodiment of the invention. Each selected group comprises two channels, and the channel with the greatest amplitude is selected. The cycle repetition rate is R/6 which is equal to example 2. However, an advantage over the N-of-M (example 2) is that permanent activity in all cochlear regions may be realized, comparable to standard CIS (Example 1). For example, in standard CIS, channels 1 and 2 are updated with a rate R/12, respectively. Assuming considerable spatial channel interaction between neighboring channels, the "cochlear region" associated to channels 1 and 2 is thus updated on average by a rate of R/6. In Example 3, one of the two channels 1 or 2 is selected, and thus the associated cochlear region is also updated with R/6.

EXAMPLE 4

Figure 6:
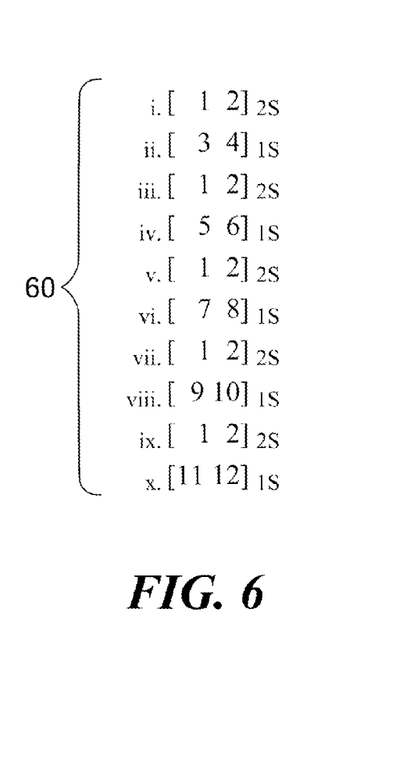
FIG. 6 shows an example of selected groups that provides good temporal representation.

In Example 4, one stimulation cycle contains ten selected groups 60, as shown in FIG. 6 in accordance with an embodiment of the invention. Group [1 2] 2S appears 5 times in one stimulation cycle, and both amplitudes are selected. The remaining selected groups contain different channels, and one maximum channel is selected. This might reflect a situation, where a good temporal representation is especially important for channels 1 and 2 (e.g., apical channels for representation of temporal fine structure), whereas the remaining channels need less temporal resolution. In this setting, channels 1 and 2 are updated with R/3, respectively, whereas the remaining "cochlear regions" are updated with R/15, respectively.

EXAMPLE 5

Figure 7:
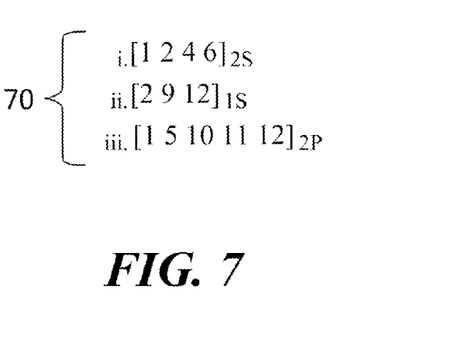
FIG. 7 shows an example of selected groups that include simultaneous stimulation.

In Example 5, a stimulation cycle includes three selected groups 70, with the two selected channels in the third group activated simultaneously (i.e., in parallel using simultaneous pulses), as shown in FIG. 7 in accordance with an embodiment of the invention. Applying simultaneous pulses advantageously maximizes data transfer time, saving time compared to a sequential pulse sequence. The amplitudes of the simultaneously activated channels in the third group may take into account parameters of spatial channel interaction, and are not limited to channels that have no or minimal spatial channel interaction. Note that a stimulation cycle may include any combination of simultaneous pulses and/or sequential pulses.

In example 5, the selected channels in the first two groups are activated sequentially, with the third group being activated simultaneously.

As described in U.S. Pat. No. 6,594,525, the simultaneous pulses described in Example 5 may be, without limitation, sign-correlated. As described above, spatial channel interaction means that there is considerable geometric overlapping of electrical fields at the location of the excitable nervous tissue, if different stimulation electrodes (positioned in the scala tympani) are activated. Due to conductivity in the scala tympani, simultaneous stimulation of two or more electrodes against a remote ground electrode generally results in a temporal mixture of constructive and destructive superposition of electrical fields at the position of the neurons. For example, if two simultaneous stimulation channels produce currents with equal amplitudes, but different signs, most of the current will flow through the shunt conductance between the two electrodes and will not reach the intended neurons. This additional effect can be removed, if "sign-correlated" pulses are employed. Sign correlated here means that if two or more pulses occur simultaneously at different electrodes, positive and negative phases are absolutely synchronous in time. This ensures that the sum of the magnitudes of the single stimulation currents is forced to flow into the reference electrode. Thus, at the site of the excitable neurons, only constructive superposition of currents is possible. The stimulation currents in the sign-correlated pulses may be determined, without limitation, such that at least the potentials at the position of the electrodes are equal as in the case of single channel stimulation. In various embodiments, it may be assumed that a single electrode causes exponential decays of the potentials at both sides of the electrode, allowing for a computationally efficient calculation of the pulse amplitudes, since a tri-diagonal matrix is involved.

Further specific embodiments of the invention take into account fundamental principles of auditory system response in normal hearing, where the frequency of a given tone affects both the cochlear location where neural response occurs and the temporal characteristics of that neural response. For complex sounds, spectral content is represented in the distribution of cochlear locations where neural responses occur, with the temporal structure of each response being associated with certain spectral components of the sound.

At low intensity levels (low volume), the basilar membrane is relatively sharply tuned so that each nerve fiber ideally picks up the sound component at the characteristic frequency (CF) of the nerve fiber and the temporal response pattern of the nerve fiber also reflects CF. At higher intensity levels (higher volume), however, the basilar membrane exhibits non-linear response with grouping of nerve fibers according to a dominant spectral component in the sound stimulus that is independent of the individual nerve fiber CFs within a group. For example, in response to a speech stimulus, responses of groups of fibers are dominated by a single formant as described in H. E. Secker-Walker and C. L. Searle, *Time-Domain Analysis Of Auditory-Nerve-Fiber Firing Rates*, J. Acoust. Soc. Am. 88:1427-1436, (1990), hereby incorporated by reference. Within each group, all fibers respond to a certain formant ($F_0$ (pitch frequency), $F_1$, $F_2$, $F_3$) of the sound stimulus with maximum responses occurring at $F_0$ across all groups. The process can also be explained in reverse—for high stimulus levels, nerve fibers are organized in groups with each group being dominated by a certain feature in the sound stimulus. As stimulus intensity decreases, group size also decreases so that more groups are formed. At low levels, each group ideally consists of nerve fibers which respond to the CF component of the stimulus. Thus nerve fibers respond in groups, with the group size being a function of stimulus intensity as determined by the nonlinear properties of the basilar membrane. Within each group, responses follow a certain dominant feature of the stimulus with the response pattern being amplitude modulated with $F_0$.

Accordingly, some specific embodiments of the present invention reflect the physiological processes discussed above and the grouping of nerve fibers according to sound stimulus intensity. Varying the number of stimulated electrodes with stimulation level can better model normal hearing. Without restricting generality, the physiological processes in normal hearing can be modeled by a stimulation definition stage (SDS) based on the non-linear properties of the basilar membrane and the adaptive function of the inner hair cells. For example, as illustrated by the example shown in FIG. 8, based on the input sound signal characteristics (C), the SDS would define G stimulation groups (with $G \leq M$) and assign the M electrode channels to the G groups, and also would define a stimulation amplitude A for each of the G stimulation groups. As an example, for a given input signal at small levels, G=M. For the same signal at higher levels, however, G<M, for example. Other algorithms are also possible, for example, deriving the number of groups and the size of each group as a function of input sound signal characteristics (C) according to a pre-determined relation between the quantities. The SDS would work continuously so that the output of the SDS—e.g., G and A—at each point in time reflects the input sound signal characteristics (C).

Figure 8:
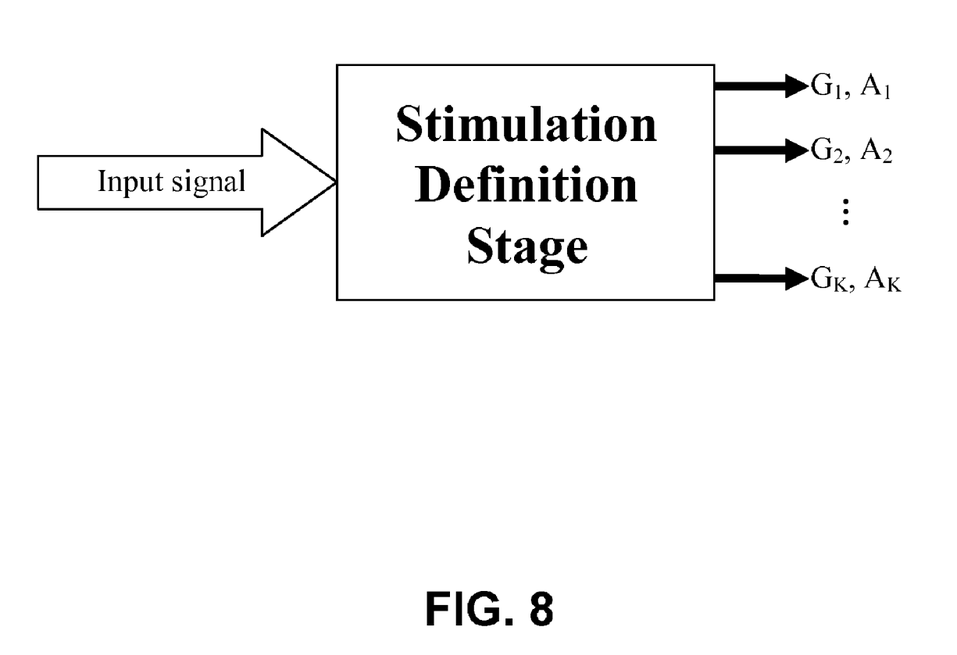
FIG. 8 shows inputs and outputs of a stimulation definition stage according to an embodiment of the present invention.

In each group, stimulation pulses can be either applied at a constant rate or at a group-specific rate. The group-specific rate could be derived from an appropriate combination of stimulus features. For example, all electrodes within a group could be stimulated at the formant frequency $F_x$ (x=0,1, 2, . . . ) the group is associated with. However, for high formant frequencies this could result in stimulation rates which might be greater than a pitch saturation limit at which pitch may not be effectively coded (around 1000 pps). Thus, as a further example, the electrodes belonging to a certain group could (in random or deterministic order) be stimulated at a rate derived from $F_x$ and the number of electrodes in the group so that the electrode-specific rate is below a certain pitch saturation limit and the aggregate group rate equals $F_x$.

Within each electrode group, channels are stimulated using the stimulation amplitude function A, which can, for example, define a constant stimulation amplitude across the group, or, as another example, define a stimulation profile. The stimulation profile could, e.g., also be derived from the non-linear properties of the basilar membrane and the adaptive function of the inner hair cells. The profile could also reflect other aspects of electrical stimulation of the cochlea, like, e.g., channel interactions. To keep interactions between adjacent groups low, smaller amplitudes could be used at the edges of a group than in the center of a group.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of activating electrodes in an implanted electrode array with a stimulation signal, the method comprising:
    for each of a plurality of defined sound signal characteristics (C) that vary over time, assigning each electrode to one of a plurality of stimulation groups (G) each having an associated group stimulation amplitude function (A), where the stimulation groups (G) and the electrodes assigned to them vary over time with the sound signal characteristics (C); and
    activating each electrode as the stimulation signal varies based on spectral components of the stimulation signal.

2. A method according to claim 1, wherein activating each electrode is further based on electrode location.

3. A method according to claim 1, wherein activating each electrode is further based on a stimulation group pulse rate defined for each stimulation group.

4. A method according to claim 1, wherein the group stimulation amplitude function (A) for each stimulation group has a constant value.

5. A method according to claim 1, wherein the group stimulation amplitude function (A) for each stimulation group reflects non-linear response characteristics of tissue stimulated by each electrode.

6. A method according to claim 1, wherein the group stimulation amplitude function (A) reflects spatial interaction between the electrodes.

7. A method according to claim 1, wherein the implanted electrode array is part of a cochlear implant system.

8. A system for activating electrodes in an implanted electrode array with a stimulation signal, the system comprising:
    a stimulation definition stage that, for each of a plurality of defined sound signal characteristics (C) that vary over time, assigns each electrode to one of a plurality of stimulation groups (G) each having an associated group stimulation amplitude function (A), where the stimulation groups (G) and the electrodes assigned to them vary over time with the sound signal characteristics (C); and an electrode stimulator for activating each electrode as the stimulation signal varies based on spectral components of the stimulation signal.

9. A system according to claim 8, wherein activating each electrode is further based on electrode location.

10. A system according to claim 8, wherein activating each electrode is further based on a stimulation group pulse rate defined for each stimulation group.

11. A system according to claim 8, wherein the group stimulation amplitude function (A) for each stimulation group has a constant value.

12. A system according to claim 8, wherein the group stimulation amplitude function (A) for each stimulation group reflects non-linear response characteristics of tissue stimulated by each electrode.

13. A system according to claim 8, wherein the group stimulation amplitude function (A) reflects spatial interaction between the electrodes.

14. A system according to claim 8, wherein the implanted electrode array is part of a cochlear implant system.

15. A non-transitory computer program product for use on a computer system for activating electrodes in an implanted electrode stimulator with a stimulation signal, the computer program product comprising a computer usable medium having computer readable program code thereon, the computer readable program code including:

program code for, for each of a plurality of defined sound signal characteristics (C) that vary over time, assigning each electrode to one of a plurality of stimulation groups (G) each having an associated group stimulation amplitude function (A), where the stimulation groups (G) and the electrodes assigned to them vary over time with the sound signal characteristics (C); and program code for activating each electrode as the stimulation signal varies based on spectral components of the stimulation signal.

16. A non-transitory computer program product according to claim 15, wherein activating each electrode is further based on electrode location.

17. A non-transitory computer program product according to claim 15, wherein activating each electrode is further based on a stimulation group pulse rate defined for each stimulation group.

18. A non-transitory computer program product according to claim 15, wherein the group stimulation amplitude function (A) for each stimulation group has a constant value.

19. A non-transitory computer program product according to claim 15, wherein the group stimulation amplitude function (A) for each stimulation group reflects non-linear response characteristics of tissue stimulated by each electrode.

20. A non-transitory computer program product according to claim 15, wherein the group stimulation amplitude function (A) reflects spatial interaction between the electrodes.

21. A non-transitory computer program product according to claim 15, wherein the implanted electrode array is part of a cochlear implant system.

* * * * *